US00PP09739P

United States Patent [19]

Dümmen

[11] Patent Number: Plant 9,739

[45] Date of Patent: Dec. 10, 1996

[54] POINSETTIA PLANT NAMED HWD MOONLIGHT

[75] Inventor: Günter Dümmen, Rheinberg-Eversael, Germany

[73] Assignee: Dummen Jungplfanzenkulturen, Rheinberg-Eversael, Germany

[21] Appl. No.: 516,183

[22] Filed: Aug. 17, 1995

[51] Int. Cl.[6] ..... A01H 5/00

[52] U.S. Cl. ..... Plt./86.2

[58] Field of Search ..... Plt./86.2

*Primary Examiner*—James R. Feyrer

*Attorney, Agent, or Firm*—Proprietary Rights International

[57] ABSTRACT

A new and distinct cultivar of Poinsettia plant named HWD Moonlight, characterized by its creamy white flower bracts; compact growth habit; short crop time, early flowering; freely branching plant habit; and excellent postproduction longevity.

1 Drawing Sheet

The present invention relates to a new and distinct cultivar of Poinsettia plant, botanically known as *Euphorbia pulcherrima* Willd., known as the variety Duemoon, and hereinafter referred to by the cultivar name HWD Moonlight.

The new cultivar is a product of a planned breeding program conducted by the inventor in Rheinberg, Germany. The objective of the breeding program was to develop a new white variety with excellent postproduction longevity.

The new cultivar originated from a cross made by the inventor of the cultivar Regina (U.S. Plant Pat. No. 7,250, Poinsettia Plant '21-85') as the male or pollen parent with the proprietary selection 88-20-5 as the female or seed parent.

The cultivar HWD Moonlight was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Poinsetta are stabilized and reproduced true to type in successive generations of asexual reproduction.

The following traits have been repeatedly observed and are determined to be the unique characteristics of HWD Moonlight. These characteristics in combination distinguish HWD Moonlight as a new and distinct cultivar:

1. Creamy white flower bracts.
2. Compact growth habit.
3. Short crop time.
4. Freely branching plant habit.
5. Excellent postproduction longevity.

In comparison to the parent cultivar Regina, the new Poinsettia is more compact in plant habit; has creamy white flower bracts versus white flower bracts; has flower bracts that overlap each other whereas the flower bracts of the cultivar Regina do not overlap giving an open appearance; and has longer postproduction longevity as foilage and cyathia are retained longer on the new Poinsettia compared to the cultivar Regina. In comparison to the parent selection 88-20-5, the new Poinsettia has whiter flower bract color; is slightly more vigorous; and flowers earlier.

The accompanying colored photograph illustrates the overall appearance of the new cultivar, showing the colors as true as it is reasonably possible to obtain in colored reproductions of this type. The photograph comprises a top perspective view of a typical potted plant of HWD Moonlight with one pinched plant in a 15-cm container. The flower bract color appears darker in the photograph due to light reflectance.

The cultivar HWD Moonlight has not been observed under all possible environmental conditions. The phenotype may vary somewhat with variations in environment such as temperature, daylength and light intensity, without, however, any variance in genotype. The following observations, measurements and comparisons describe plants grown in Rheinberg, Germany, under commercial practice in a glass-covered greenhouse with day temperatures of 22° C. and night temperatures of 18° C. and light levels of 30,000 to 40,000 lux.

In the following description, color references are made to The Royal Horticultural Society Colour Chart except where general terms of ordinary dictionary significance are used.

Classification:

*Botanical.*—*Euphorbia pulcherrima* Willd.

*Commercial.*—Poinsettia.

*Cultivar.*—'HWD Moonlight'.

Parentage

*Male parent.*—'Regina' (U.S. Plant Pat. No. 7,250, Poinsettia Plant '21-85').

*Female parent.*—Proprietary selection 88-20-5.

Propagation:

*Type cutting.*—Terminal cuttings.

*Time to initiate roots.*—Summer: 27° C., 21 days; winter: 20° C., 28 days,

*Rooting habit.*—Fine, freely branching.

Plant description:

*Plant form.*—Vase-shaped.

*Growth habit.*—Freely branching and upright. Branching is enhanced by the removal of the apical shoot tip. Compact growth habit.

*Foliage description.*—Arrangement: Opposite. Size: Length: 9 to 10 cm. Width: 6.5 to 8 cm. Shape: Ovate. Tip: Acuminate. Base: Acute. Margin: Entire and sometimes lobed. Texture: Upper side: Glabrous. Under side: Pubescent at veins, very fine pubescence. Color: Young foliage upper side: 137B. Young foliage under side: 138A. Mature foliage top side: Darker than 137B. Mature foilage under side: 138A. Venation: Upper side: 144B. Under side: 144B, prominent. Petiole: Pattern: Pinnate. Length: 4 cm. Color: 144B.

Flower description:

*Inflorescence type and habit.*—Inflorescences are compound corymbs or cyathia with colored flower bracts subtending the cyathia.

*Natural flowering season.*—Autumn/winter in Northern Hemisphere. Flower initiation and development can be induced under short day/long night conditions.

*Time to flower.*—8 weeks under short day/long night conditions.

*Quantity of inflorescences.*—10 to 15 cyathia per corymb.

*Inflorescence size.*—Diameter: 22 cm. Height (depth): 7 cm.

*Flower bracts.*—Attitude: Horizontal to stem axis. Quantity of flower bracts: 15 per influorescence. Size: Length: 11.5 to 13 cm. Width: 6.5 to 10 cm. Shape: Elliptic. Tip: Acuminate. Base: Acute. Margin: Usually lobed, sometimes entire. Texture: Upper side: Satiny, glabrous. Under side: Smooth, glabrous. Color: When opening: 2D. Mature, top side: 2D. Mature, under side: 1D. Fading to: Flower bract color does not fade. Venation: Upper side: 2D. Under side: 1D. Petiole: Length: 15 to 17 cm. Color: 137C.

*Cyathia.*—Quantity: 10 to 15 per corymb. Color, immature and mature: 144A. Diameter of cyathia cluster: 3.5 cm. Stamens: Stamen number: 10 to 25 per cyathium. Anther size: 0.5 mm. Anther color: 155D. Pollen color: 12B. Pistils: Pistil number: 1 per cyathium. Stigma color: 145A. Style color: 145A. Style length: 4 mm. Ovary number: 3. Nectaries: Usually one or two per cyathium.

Disease resistance: No fungal, bacterial nor viral problems observed.

Postproduction longevity: Generally more than 4 weeks under interior conditions.

It is claimed:

1. A new and distinct cultivar of Poinsettia plant named HWD Moonlight, as illustrated and described.

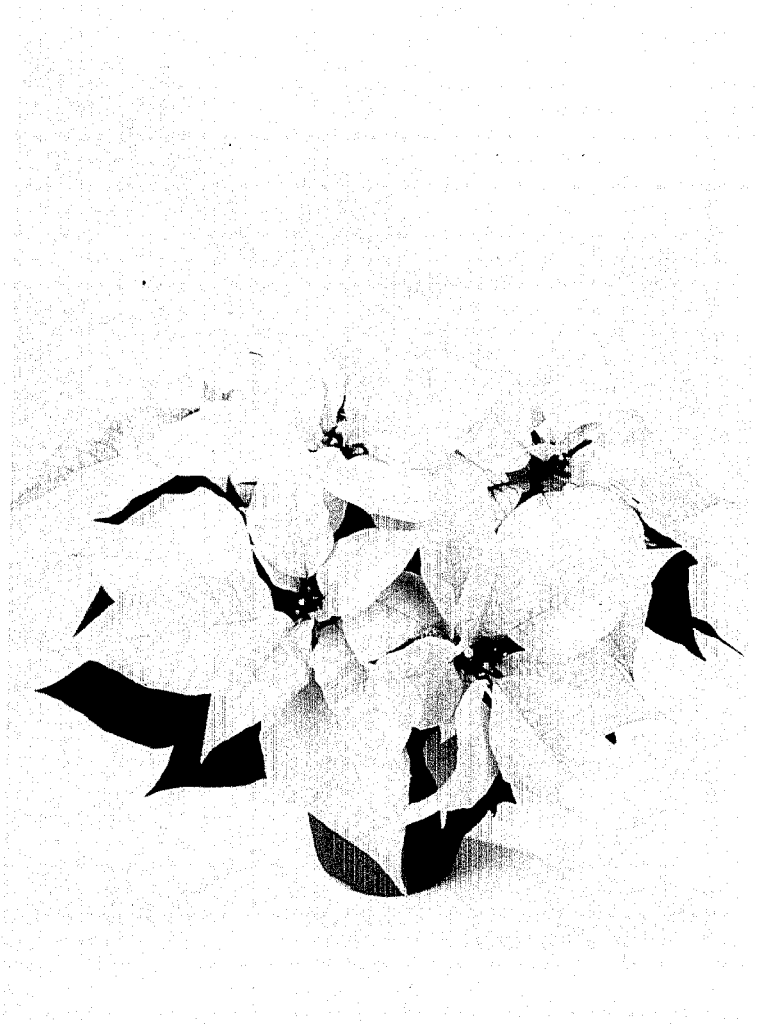

* * * * *